United States Patent [19]

Pruss

[11] Patent Number: 5,698,537
[45] Date of Patent: Dec. 16, 1997

[54] METHOD OF LOWERING THE VISCOSITY OF MUCUS

[75] Inventor: Thaddeus P. Pruss, Madison, Wis.

[73] Assignee: Clarion Pharmaceuticals Inc., Madison, Wis.

[21] Appl. No.: 666,631

[22] Filed: Jun. 18, 1996

[51] Int. Cl.$^6$ .............................................. A61K 31/685
[52] U.S. Cl. .................. 514/78; 514/77; 514/826; 514/851; 514/855
[58] Field of Search .................... 514/77, 78, 825, 514/851, 855

[56] References Cited

U.S. PATENT DOCUMENTS

| | | | |
|---|---|---|---|
| 4,312,860 | 1/1982 | Clements | 424/199 |
| 4,571,334 | 2/1986 | Yoshida et al. | 424/95 |
| 4,622,180 | 11/1986 | Paltauf et al. | 260/389 |
| 4,765,987 | 8/1988 | Bonte et al. | 424/450 |
| 4,814,112 | 3/1989 | Paltauf et al. | 260/403 |
| 5,262,405 | 11/1993 | Girod-Vaquez et al. | 514/75 |
| 5,299,566 | 4/1994 | Davis et al. | 128/200.24 |

OTHER PUBLICATIONS

Galabert et al., Relationships between the lipid content and the rheological properties of airway secretions in cystic fibrosis, *Clinica Chimica Acta* (1987), 164:139–149.
Hansen et al., *Lipids* (1982), 17, 453–459.
Murari et al., *J. Org. Chem.*, (1982), 47, 2158–2163.
Lammers et al., *Chem. Phys. Lipids* (1978), 22, 293–305.
Eibl et al., *Liebigs Ann. Chem.* (1967), 709, 226–230.
Okazaki et al., *Bull. Chem. Soc. Jpn.* (1981), 54, 2399–2407.
Chand et al. (1993), *Agents and Actions*, 38, 165–170.
American Thoracic Society, Symposia Excerpts, 1994 International Conference.
Ferguson and Chermiack (1993) Management of COPD, *New. Eng. J. Med.*, pp. 1017–1021.

*Primary Examiner*—Kimberly Jordan
*Attorney, Agent, or Firm*—DeWitt Ross & Stevens, S.C.; Salvatore R. Conte, Esq.

[57] ABSTRACT

The use of phospholipids of the following formula to reduce the viscosity of mucus in a patient is described:

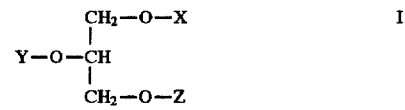

wherein one of X, Y, or Z represent:

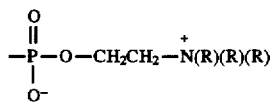

in which each R represents hydrogen or methyl, and each of the other two of X, Y, or Z represents —CO—R$^1$ in which R$^1$ represents linear or branched $C_{11-21}$ alkyl or $C_{11-21}$ alkenyl, unsubstituted or substituted with one or more substituents selected from the group consisting of halo, $C_{1-6}$ linear or branched alkoxy or cyano.

12 Claims, No Drawings

METHOD OF LOWERING THE VISCOSITY OF MUCUS

FIELD OF THE INVENTION

The present invention is in the field of mucolysis and, in particular, it relates to the uie of certain mucolytic agents in thinning or lowering the viscosity of tenacious mucus, a viscid secretion of the mucous membranes. By reducing the viscosity of mucus secretions, such agents increase the efficiency of the cough reflex and of ciliary action in removing accumulated mucous secretions from the lung airways.

DESCRIPTION OF THE PRIOR ART

There are several reported drugs which have been shown to have a beneficial effect on airway clearance of mucus, for example, through their effect on cilia or by altering the physical properties of mucous secretions. One class, represented by iodides, for example, a saturated solution of potassium iodide, or iodinated glycerol, is thought to stimulate the secretion of "thinner" secretions that are easier to clear. Another class is represented by N-acetyl cysteine. The viscosity of pulmonary mucous secretions depends largely on the concentrations of mucoprotein, and the free sulfhydryl groups in N-acetyl cysteine have been thought to open mucoprotein disulfide bonds, thereby reducing the viscosity of mucus. For a review of mucolytic drugs, see the book by P. C. Braga: *Drugs in Bronchial Mucology*, Raven Press, New York, 1989.

SUMMARY OF THE INVENTION

It is an object of the present invention to provide a method of reducing the viscosity of pulmonary mucus.

It is another object of the present invention to improve removal of accumulated mucus in patients with excessive mucous secretions.

It is a further object of the present invention to provide a method of ameliorating a variety of pulmonary disorders involving airway obstruction due to accumulated mucous secretions.

It has now been found, without being bound to any particular mode of action, that the following phospholipids of Formula I demonstrate marked mucolytic activity:

```
     CH2—O—X
     |
Y—O—CH
     |
     CH2—O—Z
```
I wherein one of X, Y, or Z represents:

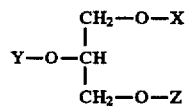

in which each R group independently represents hydrogen or methyl (the compound wherein all three R groups are methyl is preferred); and each of the other two of X, Y, or Z independently represents —CO—R¹ in which R¹ represents linear or branched $C_{11-21}$ alkyl or $C_{11-21}$ alkenyl, unsubstituted or substituted with one (preferred) or more substituents selected from the group consisting of halo (i.e., fluoro, bromo, chloro, or iodo) and $C_{1-6}$ linear or branched alkoxy or cyano. Preferably, the two —CO—R¹ groups are identical.

The subject phospholipids of Formula I contain an optically active carbon at the 2-position of the glycerol backbone. All optical isomers, including those having an optical center present in the side chain R¹, are contemplated by the present invention. Also included are geometrical isomers which result when R¹ is alkenyl.

The preferred phospholipids of Formula I are represented by Formula II:

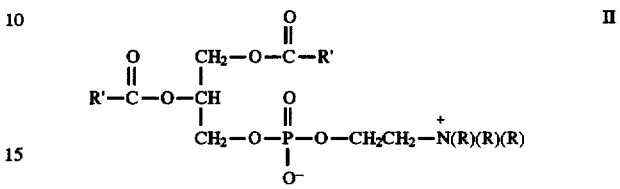

wherein R and R¹ are as previously defined; and all isomeric forms thereof.

The most preferred phospholipids of Formula I are dipalmitoyl phosphatidylcholine (DPPC), also identified as 1,2-dipalmitoyl-sn-glycero-3-phosphocholine, and distearoyl phosphatidylcholine (DSPC), also identified as 1,2-distearoyl-sn-glycero-3-phosphocholine. The naturally occurring isomer of DPPC is dipalmitoyl-L-alpha-phosphatidylcholine.

Other representative phospholipids of Formula I include:

1,2-dipalmitoyl-sn-glycero-3-phosphoethanolamine;
1,3-dipalmitoyl-sn-glycero-2-phosphocholine;
1,2-distearoyl-sn-glycero-3-phospho-(N-methyl) ethanolamine;
1-palmitoyl-2-oleoyl-sn-glycero-3-phosphocholine;
1,3-distearoyl-sn-glycero-2-phospho-(N,N-dimethyl) ethanolamine;
1,2 - dilauroyl- sn-glycero -3 -phosphocholine;
1,2-dieicosanoyl-sn-glycero-3-phosphocholine;
1-oleoyl-3-myristoyl-sn-glycero-3-phospho-(N-methyl) ethanolamine;
1,2-di-(9-chloro-octadecanoyl)-sn-glycero-3-phosphocholine;
1,2-di-(9-octadecenoyl)-sn-glycero-3-phosphocholine;
1,2-di-(8-cyano-hexadecanoyl)-sn-glycero-3-phosphocholine;
1,3-di-(9-hexadecenoyl)-sn-glycero-2 -phosphocholine; and
1,2-di-(8-methoxy-hexadecanoyl)-sn-glycero-2-phosphocholine.

DETAILED DESCRIPTION OF THE INVENTION

The phospholipids of Formula I and their methods of preparation are known in the literature and several are commercially available, including the most preferred DPPC and DSPC. For example, see U.S. Pat. Nos. 4,814,112 and 4,622,180; Hansen et al., Lipids (1982), 17, 453–459; Murari et al., *J. Org. Chem.*, (1982), 47, 2158–2163; Lammers et al., *Chem. Phys. Lipids* (1978), 22, 293–305; Eibl et al., *Liebigs Ann. Chem.* (1967), 709, 226–230; and Okazaki et al., *Bull. Chem. Soc. Jpn.* (1981), 54, 2399–2407.

Dipalmitoyl phosphatidylcholine (DPPC) is the major component (about 80% ) of natural lung surfactant in humans. Lung surfactant is a material ordinarily secreted onto the surface of lung alveoli. It is recognized that a deficiency in lung surfactant is the cause of respiratory distress syndrome (RDS) in premature babies and infants. Although such deficiency is not the primary factor in the development of adult respiratory distress syndrome (ARDS), it may contribute significantly to the pathophysiology of the disorder.

RDS is the leading cause of death and disability among premature infants. In addition, about 150,000 cases of ARDS are reported annually with 60–80% mortality. To treat RDS and ARDS, a number of natural surfactants (human and bovine) and completely synthetic surfactants have been administered to the lungs of human subjects, for example, by inhalation of an aerosol formulation.

In general, most synthetic inhalant surfactant formulations contain DPPC, since it is known that DPPC can improve respiratory function in patients with RDS and ARDS. It does so by decreasing the surface tension of the alveoli of the lung, thereby permitting them to open more readily to exchange oxygen and carbon dioxide. See generally, for example, the disclosures of U.S. Pat. No. 5,299,566, which discloses a method for preparing a surfactant dispersion containing DPPC; U.S. Pat. No. 5,110,806, which discloses a synthetic surfactant containing DPPC, a long chain alcohol and a nonionic surfactant; U.S. Pat. No. 4,765,987, which discloses a synthetic surfactant containing DPPC, DSPC and Soya lecithin; U.S. Pat. No. 4,571,334, which discloses various drugs in combination with lung surfactant; and U.S. Pat. No. 4,312,860, which discloses a synthetic surfactant containing DPPC and a fatty alcohol. Each of the foregoing references are included herein by reference, including references cited therein.

Applicant is unaware, however, that DPPC or any other embodiment of the Formula I phospholipids have been reported as having mucolytic activity, the basis of the present invention. It has now been found that the subject phospholipids I decrease the viscosity of tenacious mucus, thereby facilitating removal of viscous, inspissated mucus from the lung airways. As a result, bronchial and tracheal drainage of mucus is improved, and congestion in acute or chronic pulmonary disorders due to excessive accumulation of mucus in the lungs and upper respiratory tract is alleviated.

The present invention thus provides a method of alleviating respiratory distress due to tenacious pulmonary mucous secretions; particularly of the non-alveolar type, i.e., in the trachea, the bronchi, and the bronchiols, in a patient suffering from such distress. The method is beneficially accomplished by the intermittent inhalation of an aerosol to deliver an effective mucolytic amount of a Formula I phospholipid to the lung airways.

The mucolytic activity of the subject phospholipids is demonstrated in standard in vitro and in vivo assays employing bovine tracheal mucus and an animal model, respectively. Regarding the in vitro assay, when bovine tracheal mucus is mixed with DPPC, DSPC or other Formula I phospholipid, the mucus is liquefied and flows more freely than when the vehicle alone (saline) is employed. The in vivo mucolytic assay is similar to that described by Chand et al. (1993), Agents and Actions, 38:165–170, incorporated herein by reference. See in particular the evaluation of mucolytic activity in mice found on page 166 et seq. A more detailed description of the foregoing in vitro and in vivo assays is provided in the Examples hereinafter. The results, exemplified by the test compound, DPPC, show mucolytic activity equivalent to the known mucolytic, N-acetylcysteine.

Aerosolized delivery of drugs to the lung airways has been employed in clinical practice for many years. A variety of medicinal agents have been utilized in aerosol therapy including, for example, mucolytics such as N-acetylcysteine and synthetic surfactant formulations containing DPPC and DSPC for treating patients with RDS and ARDS. The advantage of an aerosol delivery system is its wide-spread drug delivery to all lung regions intermittently over extended periods of time.

It is intended that the phospholipids of Formula I be utilized as a dispersion in aerosolized liquid formulations ready for use, for example, for administration with a nebulizer or a metered-dose inhaler. The subject phospholipids may also be prepared as a sterile lyophilized powder of appropriate average diameter for direct inhalation or, alternatively, the powder is reconstituted with an aqueous carrier such as water or, preferably, a saline solution of about 0.4 to about 0.9 percent sodium chloride as a dispersion and delivered via an appropriate nebulizer or inhalant system. The recommended average diameter of the particulate dispersed powder along any axis is about 1 to 10 microns ($\mu$m) and, preferably, about 5 to 10 $\mu$m. In general, the phospholipid is included in an amount from about 0.1 to 10 percent weight/volume dispersed in normal or slightly hypotonic saline with an art-recognized propellant such as, for example, dichlorodifluoromethane, presented as a metered-dose aerosol unit. Each actuation releases between 0.1 and 100 mg of the phospholipid I.

The technology for making aerolized drug delivery systems is well documented. The phospholipids of Formula I are incorporated into such systems by art-recognized methodologies which need not be repeated in detail here. Indeed, as noted previously, aerosol surfactant formulations containing DPPC and DSPC and their preparation have been previously described for treating RDS and ARDS, and similar aerosol methodologies are employed for this invention.

In accordance with the present invention, the subject phospholipids I have utility as an inhalant in the treatment of respiratory diseases in which mucous viscosity or accumulated mucus is a major problem. Such diseases may include chronic bronchitis, cystic fibrosis and asthma (see American Thoracic Society, Symposia Excerpts, 1994 International Conference). Moreover, chronic obstructive pulmonary disease is associated with increased mucous secretion (see Ferguson and Chermiack (1993) Management of COPD, New. Eng. J. Med., pp. 1017–1021). The present invention is not applicable to treating RDS or ARDS since these respiratory ailments are alveolar in nature and are not characterized by thickened or excessive mucous secretions.

The subject phospholipids I may be used alone or in combination with other mucolytics and/or other active ingredients suitable for aerosol delivery to the airways and alveoli of the lung, for example, antibiotics, bronchodilators and the like.

The following examples, employing DPPC for illustrative purposes, are intended to illustrate and not to limit the scope of the present invention.

EXAMPLE 1

Mucolytic Activity in Bovine Tracheal Mucous

Tracheal mucus is gently scraped from freshly slaughtered cows obtained from a local slaughter house. Under fixed isothermal conditions, the mucus is mixed at a ratio of 5 ml of mucus to 1 ml of physiological saline and sonicated for 1 minute. 1 milliliter of this mixture is added to 1 ml of the test compound or control saline and sonicated again for 1 minute. Five minutes after sonicating, 1 ml of sample is pipetted into the barrel of a 3-ml syringe with an 18 g×1.5 inch needle and attached vertically to a ring stand. At time zero, the needle cap is removed and the transit time for the mucus to run through the syringe/needle combination is recorded. The results are shown below:

| Compound | Final Concentration | Transit Time |
|---|---|---|
| Saline Control | Control | 3 min. 32 sec. |
| DPPC | 5 mg/ml | 2 min. 20 sec. |

The results indicate that DPPC has a direct mucolytic effect on bovine tracheal mucus. Similar results are obtained with DSPC.

EXAMPLE 2

Mucolytic Activity in Mouse Tracheal Mucous

The procedure, which delivers the test compound to mice as an aerosol, is a modified assay for the evaluation of mucolytic activity in mice described by Chand et al., previously cited.

1. The test animals are Hsd:1CR(CD-1) mice that weigh approximately 25 g each.
2. The test compound is diluted in normal saline to a concentration of 25 mg/ml and administered using a human De Vilbiss atomizer Model No. 15 at approximately 100 mg/kg. The control group receives saline. The nozzle is placed in the mouth of the mouse and 2 spray doses are given.
3. After 30 minutes, phenol red dissolved as a 5% solution in saline is given IP at a dose of 0.1 ml/10 g body weight.
4. Thirty minutes after phenol red administration, the animals are sacrificed by exposure to 100% $CO_2$.
5. The entire trachea is removed, the exterior blotted dry and the trachea washed in 1.0 ml saline. 30 Minutes later, 0.1 ml of 1M NaOH is added to the tracheal washings to stabilize the pH of the lavage fluid.
6. The amount of phenol red secreted into the trachea is quantitated photometrically at 546 nm.
7. Calibration of the dose delivered is done by measuring the volume of five sprays per tube in five separate tubes. The average amount is 60.4 µl/spray with a range of 58–63 µl.

The test results indicate that the measured percent change in mucolytic activity for DPPC is about 58 percent, as compared to about 62 percent for N-acetylcysteine and zero percent for the saline control.

EXAMPLE 3

Inhalation Cartridge

| Inhalation Cartridge | |
|---|---|
| Component | Amount per Cartridge |
| DPPC | 5.0 mg |
| Lactose, q.s. | 25.0 mg |

The active ingredient, DPPC, premicronized to a particle size between 10–50 microns in average diameter, is blended with normal tabletting grade lactose in a high energy mixer. The powder blend is micronized to a fine particle size between 1–10 microns and filled into appropriately sized hard gelatin capsules or cartridges on a suitable encapsulating machine. The respirable contents of the capsules or cartridges are administered using a powder inhaler.

EXAMPLE 4

Metered Liquid Dose

| Metered Liquid Dose | |
|---|---|
| Component | Amount per Cartridge |
| DPPC | 5.0% by weight |
| isotonic saline | q.s. |

The active ingredient, DPPC, is dissolved in a sufficient quantity of sterile, isotonic saline to yield a solution which is 5% by weight DPPC. The solution is administered in the form of an aerosolized metered-dose via a suitable nebulizing device.

What is claimed is:

1. A method of reducing the viscosity of mucus in a patient ailing from a pulmonary disorder involving thickened or accumulated mucous secretions which comprises delivering to the lung airways of such patient an effective mucolytic amount of a phospholipid of the following formula in the form of an aerosol:

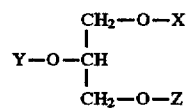

wherein one of X, Y, or Z represent:

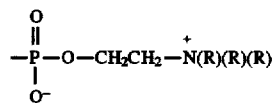

in which each R represents hydrogen or methyl, and each of the other two of X, Y, or Z represents —CO—$R^1$ in which $R^1$ represents linear or branched $C_{11-21}$ alkyl or $C_{11-21}$ alkenyl, unsubstituted or substituted with one or more substituents selected from the group consisting of halo, $C_{1-6}$ linear or branched alkoxy or cyano; and all isomeric forms thereof.

2. The method of claim 1, wherein a phospholipid of the following formula is delivered to the lung airways of the patient:

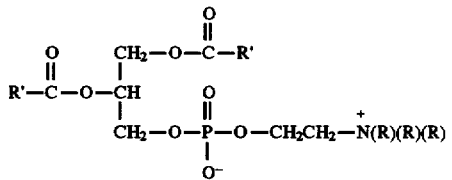

wherein each R represents hydrogen or methyl, and $R_1$ represents linear or branched $C_{11-21}$ alkyl or $C_{11-21}$ alkenyl, unsubstituted or substituted with one or more substituents selected from the group consisting of halo, $C_{1-6}$ linear or branched alkoxy or cyano; and all isomeric forms thereof.

3. The method of claim 1, wherein said phospholipid is dipalmitoyl or distearoyl phosphatidylcholine.

4. The method of claim 1 wherein said phospholipid is dipalmitoyl phosphatidylcholine.

5. A method of reducing the viscosity of mucus in a patient ailing from a pulmonary disorder involving thickened or accumulated mucous secretions which comprises delivering to the lung airways of such patient an effective mucolytic amount of a phospholipid of the following formula in the form of an aerosolized powder:

$$\begin{array}{c} CH_2-O-X \\ | \\ Y-O-CH \\ | \\ CH_2-O-Z \end{array} \qquad I$$

wherein one of X, Y, or Z represents:

$$\begin{array}{c} O \\ \| \\ -P-O-CH_2CH_2-\overset{+}{N}(R)(R)(R) \\ | \\ O^- \end{array}$$

in which R represents hydrogen or methyl, and each of the other two of X, Y, or Z represents —CO—$R^1$ in which $R^1$ represents linear or branched $C_{11-21}$ alkyl or $C_{11-21}$ alkenyl, unsubstituted or substituted with one or more substituents selected from the group consisting of halo, $C_{1-6}$ linear or branched alkoxy or cyano; and all isomeric forms thereof.

6. The method of claim 5 wherein said phospholipid is dipalmitoyl or distearoyl phosphatidycholine.

7. The method of claim 5 wherein said phospholipid is dipalmitoyl phosphatidylcholine.

8. A method of reducing the viscosity of mucus in a patient ailing from a pulmonary disorder involving thickened or accumulated mucous secretions which comprises delivering to the lung airways of such patient an effective mucolytic amount of a phospholipid of the following formula in the form of an aerosolized powder:

$$\begin{array}{c} \quad\quad\quad\quad O \\ \quad\quad\quad\quad \| \\ \quad\quad\quad CH_2-O-C-R' \\ O \quad\quad | \\ \| \quad\quad | \\ R'-C-O-CH \quad\quad O \\ \quad\quad | \quad\quad \| \\ \quad\quad CH_2-O-P-O-CH_2CH_2-\overset{+}{N}(R)(R)(R) \\ \quad\quad\quad\quad | \\ \quad\quad\quad\quad O^- \end{array} \qquad II$$

wherein each R represents hydrogen or methyl, and $R^1$ represents linear or branched $C_{11-21}$ alkyl or $C_{11-21}$ alkenyl, unsubstituted or substituted with one or more substituents selected from the group consisting of halo, $C_{1-6}$ linear or branched alkoxy or cyano; and all isomeric forms thereof.

9. A method of reducing the viscosity of mucus in a patient ailing from a pulmonary disorder involving thickened or accumulated mucous secretions which comprises delivering to the lung airways of such patient an effective mucolytic amount of a phospholipid of the following formula in the form of an aerosolized liquid:

$$\begin{array}{c} CH_2-O-X \\ | \\ Y-O-CH \\ | \\ CH_2-O-Z \end{array} \qquad I$$

wherein one of X, Y, or Z represents:

$$\begin{array}{c} O \\ \| \\ -P-O-CH_2CH_2-\overset{+}{N}(R)(R)(R) \\ | \\ O^- \end{array}$$

in which R represents hydrogen or methyl, and each of the other two of X, Y, or Z represents —CO—$R^1$ in which $R^1$ represents linear or branched $C_{11-21}$ alkyl or $C_{11-12}$ alkenyl, unsubstituted or substituted with one or more substituents selected from the group consisting of halo, $C_{1-6}$ linear or branched alkoxy or cyano; and all isomeric forms thereof.

10. The method of claim 9 wherein said phospholipid is dipalmitoyl or distearoyl phosphatidycholine.

11. The method of claim 9 wherein said phospholipid is dipalmitoyl phosphatidylcholine.

12. A method of reducing the viscosity of mucus in a patient ailing from a pulmonary disorder involving thickened or accumulated mucous secretions which comprises delivering to the lung airways of such patient an effective mucolytic amount of a phospholipid of the following formula in the form of an aerosolized liquid:

$$\begin{array}{c} \quad\quad\quad\quad O \\ \quad\quad\quad\quad \| \\ \quad\quad\quad CH_2-O-C-R' \\ O \quad\quad | \\ \| \quad\quad | \\ R'-C-O-CH \quad\quad O \\ \quad\quad | \quad\quad \| \\ \quad\quad CH_2-O-P-O-CH_2CH_2-\overset{+}{N}(R)(R)(R) \\ \quad\quad\quad\quad | \\ \quad\quad\quad\quad O^- \end{array} \qquad II$$

wherein each R represents hydrogen or methyl, and $R^1$ represents linear or branched $C_{11-21}$ alkyl or $C_{11-21}$ alkenyl, unsubstituted or substituted with one or more substituents selected from the group consisting of halo, $C_{1-6}$ linear or branched alkoxy or cyano; and all isomeric forms thereof.

\* \* \* \* \*